(12) United States Patent
Slater et al.

(10) Patent No.: US 6,273,851 B1
(45) Date of Patent: Aug. 14, 2001

(54) RADIOACTIVE THERAPEUTIC SEEDS

(75) Inventors: Charles R. Slater, Fort Lauderdale; Scott L. Jahrmarkt, Miami Beach; Scott T. Smith, Miami; Thomas O. Bales; Kevin W. Smith, both of Coral Gables, all of FL (US)

(73) Assignee: Syntheon, LLC, Miami, FL (US)

( * ) Notice: Subject to any disclaimer, the term of this patent is extended or adjusted under 35 U.S.C. 154(b) by 0 days.

(21) Appl. No.: 09/312,215

(22) Filed: May 14, 1999

Related U.S. Application Data (63) Continuation-in-part of application No. 09/133,081, filed on Aug. 12, 1998, now Pat. No. 6,080,099.

(51) Int. Cl.⁷ .............................. A61M 36/00; A61N 5/00
(52) U.S. Cl. ......................................... 600/8; 600/3
(58) Field of Search .............................................. 600/1–8

(56) References Cited

U.S. PATENT DOCUMENTS

| | | | |
|---|---|---|---|
| 3,351,049 | 11/1967 | Lawrence | 128/1.2 |
| 4,323,055 | 4/1982 | Kubiatowicz | 128/1.2 |
| 4,697,575 | 10/1987 | Horowitz | 128/1.2 |
| 4,702,228 | 10/1987 | Russell, Jr. et al. | 128/1.2 |
| 4,754,745 | 7/1988 | Horowitz | 128/1.2 |
| 4,819,618 | 4/1989 | Liprie | 600/7 |
| 4,891,165 | 1/1990 | Suthanthiran | 252/633 |
| 4,994,013 | 2/1991 | Suthanthiran | 600/8 |
| 5,342,283 | 8/1994 | Good | 600/8 |
| 5,405,309 | 4/1995 | Carden, Jr. | 600/3 |
| 5,460,592 | 10/1995 | Langton et al. | 600/7 |
| 5,713,828 | 2/1998 | Coniglione | 600/7 |
| 6,010,446 | * 1/2000 | Grimm | 600/7 |
| 6,016,439 | * 1/2000 | Acker | 600/414 |
| 6,099,458 | * 2/1998 | Robertson | 600/8 |

* cited by examiner

*Primary Examiner*—John P. Lacyk
(74) *Attorney, Agent, or Firm*—David P Gordon; David S Jacobson; Thomas S Gallagher (57) ABSTRACT

Radioactive therapeutic seeds include a substantially radiotransparent cylindrical capsule containing a radioactive isotope and, in particular embodiments, a radiopaque or MRI-visible marker. Each of the embodiments is designed to provide a substantially isotropic distribution of radiation. In one embodiment, the isotope is deposited on the outer surface of a hollow radiolucent tube and a collar is provided about a central portion of the tube. The capsule comprises two tubular halves positioned over the tube with the open ends of the halves forming an interference fit with the collar and welded thereabout. In another embodiment, the isotope bearing structure is a plurality of radiolucent spheres provided with a thin coating of silver to facilitate the adhesion of the isotope thereto. The spheres are provided in two capsule halves which are welded closed about a plug have an axial radiopaque marker therein. In yet another embodiment, the isotope bearing structure is a pair of silver tubes having surfaces on which the isotope is provided. One tube is positioned in each half of the capsule, and the halves are then welded about a plug provided with a marker. In each embodiment, the closed ends of the capsule are provided with tissue engaging members or connectors which can be coupled to discrete spacing links.

39 Claims, 5 Drawing Sheets

RADIOACTIVE THERAPEUTIC SEEDS

This application is a continuation-in-part of U.S. Ser. No. 09/133,081, filed Aug. 12, 1998, now U.S. Pat. No. 6,080,099 which is hereby incorporated by reference herein in its entirety.

BACKGROUND OF THE INVENTION

1. Field of the Invention

The invention relates to radioactive therapeutic seeds. More particularly, the invention relates to improved radioactive therapeutic seeds for the treatment of oncological and other medical conditions.

2. State of the Art

Radioactive seed therapy is a well known and well accepted medical procedure for the treatment of various oncological and other medical conditions. Seed therapy, also known as brachytherapy typically involves the implantation of fifty to one hundred tiny capsules (seeds) into or around a treatment site. The capsules contain a radioactive isotope which irradiates the treatment site at close range without adversely affecting other parts of the body. Brachytherapy has been used successfully in the treatment of various types of cancers such as prostate cancer. It has also been used to prevent the growth or regrowth of tissues in the treatment of various occlusive diseases such as arteriosclerosis and arthrosclerosis subsequent to balloon angioplasty.

Radioactive therapeutic seeds are carefully designed to possess several important qualities. First, they are relatively small, typically approximately 0.025 inch in diameter and approximately 0.16 inch long so that they may be implanted using minimally invasive instruments and techniques. Second, the radioactive isotope must be enclosed in a biocompatible protective package since the seeds are typically not removed and will remain in the body for many years. Third, each seed preferably includes a radiopaque (e.g. high Z material) marker so that it can be located at the treatment site with the aid of fluoroscopy. Fourth, the protective package and the radiopaque marker preferably do not cast "shadows" in the irradiation pattern of the isotope. Fifth, the isotope should be evenly distributed within the protective package so as to avoid any "hot spots" of radiation.

The state of the art of radioactive therapeutic seeds is substantially disclosed in seven U.S. Pat. No. 5,713,828 to Coniglione for "Hollow-Tube Brachytherapy Device", U.S. Pat. No. 5,405,309 to Carden, Jr. for "X-Ray Emitting Interstitial Implants", U.S. Pat. No. 4,891,165 to Suthanthiran for "Device and Method for Encapsulating Radioactive Materials" and U.S. Pat. No. 4,784,116 to Russell, Jr. et al. for "Capsule for Interstitial Implants", U.S. Pat. No. 4,702,228 to Russell, Jr. et al. for "X-Ray Emitting Interstitial Implants", U.S. Pat. No. 4,323,055 to Kubiatowicz for "Radioactive Iodine Seed", and U.S. Pat. No. 3,351,049 to Lawrence for "Therapeutic Metal Seed Containing within a Radioactive Isotope Disposed on a Carrier and Method of Manufacture".

The Lawrence patent describes many of the essential features of radioactive therapeutic seeds. Lawrence describes radioactive isotopes (I-125, Pd-103, Cs-131, Xe-133, and Yt-169) which emit low energy X-rays and which have relatively short half-lives. When implanted at a treatment site, these isotopes provide sufficient radiotherapy without posing a radiation danger to the medical practitioner(s), people in the vicinity of the patient, or other parts of the patient's body. Lawrence further describes a protective capsule which contains the isotope and prevents it from migrating throughout the body where it might interfere with healthy tissue. The capsule is cylindrical and made of low atomic number biocompatible materials such as stainless steel or titanium which substantially do not absorb X-rays. The isotope is coated on a rod shaped carrier made of similar X-ray transparent (e.g. low Z) material and is placed inside the capsule cylinder. The ends of the capsule cylinder are closed by swaging or spinning and soldering or welding. According to a preferred embodiment, Lawrence places a radiopaque marker inside the seed. In one embodiment, the marker is a wire embedded inside the carrier rod. The wire is made of high atomic number material such as gold or tungsten which absorb X-rays.

In 1980, Kubiatowicz made a minor improvement in the basic Lawrence design by providing that the entire isotope carrier be made of radiopaque material such as silver. Kubiatowicz recognized that since the isotope was carried on the entire outer surface of the carrier, there was no need to make the carrier body X-ray transparent as suggested by Lawrence. The larger radiopaque carrier body described by Kubiatowicz makes the seeds easier to see with X-ray or fluoroscopic examination. Thus, the seeds may be placed more accurately at or around the treatment site.

Several years later, Russell, Jr. et al., in U.S. Pat. Nos. 4,707,228 and 4,784,116, explained that the capsule design of Lawrence and Kubiatowicz produces anisotropic angular radiation distribution. According to Russell, Jr. et al., the shell forming techniques used in the Lawrence-type seeds results in large beads of shell material at the ends of the seeds. These beads substantially shield radiation thereby casting shadows in the irradiation pattern of the isotope. Russell, Jr. et al. proposed a new seed design to solve this problem. In particular, Russell, Jr. et al. proposed a seed having a cylindrical container which is sealed with end caps which have a wall thickness that is substantially the same as the wall thickness of the cylindrical container. The end caps are attached to the cylindrical container by welding or crimping.

An alternate solution to the non-uniform radiation pattern of the Lawrence type seeds was proposed by Suthanthiran in U.S. Pat. No. 4,891,165. Suthanthiran's solution was to form a seed capsule from two interfitting sleeves, each having one open end and one closed end. The thickness of the sleeve side walls and their closed ends is such that when the sleeves are interfit in an overlapping manner, the total side wall thickness of the assembled capsule is approximately equal to the end wall thickness.

Other improvements in radioactive therapeutic seeds are disclosed in U.S. Pat. No. 5,405,309 which concerns a safe isotopically pure Pd-103 seed, and U.S. Pat. No. 5,713,828 which discloses a hollow tube seed which can be implanted with suture material.

Despite the fact that radioactive therapeutic seeds have been in use for over thirty years and despite the several significant improvements made in these seeds, many concerns still exist regarding their design and construction.

While significant attention has been given to the methods by which a cylindrical seed capsule is sealed, it is still difficult to seal such a small cylindrical capsule without adversely affecting the functionality of the seed. Most capsules are sealed at an end using solder which causes a shadow and consequent anisotropic radiation distribution. Radioactive therapeutic seeds are typically deployed by injection through a hollow needle into soft tissue. Upon deployment, it is desirable to position the seeds relatively quickly to minimize exposure of radiation to the physician and to minimize trauma to the patient. It is also desirable to relatively space the seeds according to the prescriptive dose of radiation to be applied at a physiological site and the concentration of the radiation. Moreover, it is desirable to relatively space apart the seeds in a manner which does not affect the distribution of radiation from the seeds.

U.S. Pat. No. 5,460,592 to Langton et al. discloses a plurality of seeds disposed in a bioabsorbable material to facilitate delivery. However, the device has several drawbacks. First, the chain of seeds linked by the bioabsorbable material has very little compression strength. Therefore, it is difficult to feed the seeds together to treatment site. Second, by disposing the seeds within the material, the effective diameter of each seed is increased by the thickness of the bioabsorbable material surrounding the seed. Yet it is desirable to restrict the diameter of each seed to as small as possible to minimize the size of needle inserted into the body and thereby minimize trauma to the patient. Additionally, U.S. Pat. No. 4,784,116 to Russel, Jr. et al. discloses utilizing discrete links to couple a plurality of seeds together end to end. However, the links couple to the seeds solely by an interference fit and, as such, are subject to failure upon the application of tensile force. Moreover, the spacers disclosed in Russel, Jr. are not bioabsorbable and remain intact in the human body, a feature which is not desirable once the seeds have been properly positioned at the treatment site.

SUMMARY OF THE INVENTION

It is therefore an object of the invention to provide radioactive therapeutic seeds which have a relatively isotropic radiation pattern.

It is also an object of the invention to provide radioactive therapeutic seeds which are easy to manufacture.

It is another object of the invention to provide radioactive therapeutic seeds which can be deployed relatively quickly and easily.

It is a further object of the invention to provide radioactive therapeutic seeds which have a structure permitting easy manipulation during and after implantation.

It is an additional object of the invention to provide radioactive therapeutic seeds which can be linked together and coherently maneuvered under both compressive and tensile forces.

In accord with these objects which will be discussed in detail below, the radioactive therapeutic seeds of the present invention include a substantially radiotransparent cylindrical capsule containing a radioactive isotope and preferably a radiopaque marker. Each of the embodiments is designed to provide a substantially isotropic distribution of radiation. As used herein, the terms "radiotransparent", "radiolucent", "radiotranslucent", and "low Z material" are used interchangeably.

According to a first embodiment of the invention, the isotope is deposited on the outer surface of a hollow radiolucent tube and a collar is preferably tightly fit about a central portion of the tube. The capsule comprises two tubular halves, each having a closed end and an open end. The halves of the capsule are positioned over the tube with the open ends of the halves being interference fit with the collar and butt welded about the centrally located collar to seal the capsule. The collar protects the contents of the capsule from the heat of welding.

According to a second embodiment of the invention, the isotope bearing structure may be one or more radiolucent particles, preferably made from titanium, aluminum or glass, and preferably spherically shaped. The particles are provided with a thin coating of silver to facilitate the adhesion of the isotope thereto. Also provided is a relatively thick tubular titanium plug having an axial radiopaque marker therein. The plug preferably includes a circumferential ridge against which the open ends of the two halves of the capsule are butt against and welded thereto.

According to a third embodiment of the invention, the isotope bearing structure is preferably a pair of silver tubes having outer and inner surfaces on which the isotope is provided. One silver tube is positioned in each half of the capsule, and the halves of the capsule are welded about a relatively thick centrally located tubular titanium plug. The plug is preferably provided with a radiopaque marker therein. In addition, the isotope bearing tube is preferably smaller than the interior of each half of the capsule, and a spacer is preferably provided in each half of the capsule between the tube and the plug to prevent relative movement of the tube within the capsule.

In each embodiment, it will be appreciated that the halves of the capsule do not overlap each other and the configuration of the capsule, isotope, and collar or plug provide the seed with a highly isotropic distribution of radiation.

In addition, the closed ends of the capsule of each seed embodiment may be provided with connectors which can be coupled to discrete spacing links to linearly align a plurality of seeds. The links are comprised of a bioabsorbable polymer, and have ends designed to securely mate with the connectors on the capsules and retain connection under both tensile and compressive forces. The capsules and links can be aligned end to end to facilitate deployment and desirable relative spacing of the capsules at the locus of treatment.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
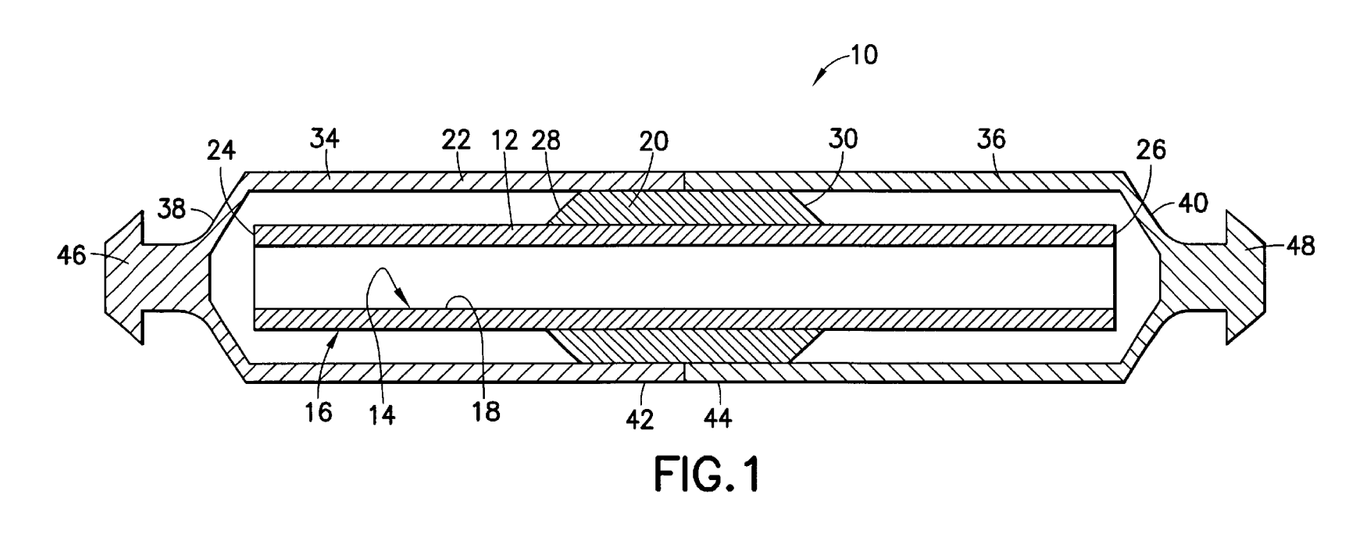
FIG. 1 is an enlarged schematic longitudinal section of a radioactive therapeutic seed according to a first embodiment of the invention.

Referring now to FIG. 1, according to a first embodiment of the invention, a radioactive therapeutic seed 10 includes an inner tube 12 having an inner surface 14 and an outer surface 16 both bearing a radioactive isotope coating 18, a collar 20 provided about a central portion of the outer surface 16 of the tube 12, and a radio transparent/translucent (low Z) capsule 22 enclosing the tube 12 and collar 18.

The inner tube 12 is preferably comprised of titanium, aluminum or other substantially radiolucent material. A silver coating is preferably provided to both the inner and outer surfaces 14, 16 to facilitate and enhance adhesion of the isotope coating 18 thereto. In the preferred embodiment, the isotope 18 does not coat the very end (longitudinal) surfaces 24, 26 of the tube 12 because such a coating has been found to undesirably affect the radiation distribution of the seed 10. The collar 20 is preferably comprised of titanium, or may be made from gold which due to its radiopaque properties will act as a marker for the seed. Additionally or alternatively, the collar 20 may be comprised of a paramagnetic or diamagnetic substance, e.g., a gadolinium metal or salt, to permit visualization of the seed with magnetic resonance imaging (MRI). It is desirable that the collar 20 be tightly formed about the tube 12. Accordingly, the collar 20 may be formed with an inner diameter greater than the outer diameter of the tube 12 and provided with a peripheral slit (not shown). The collar 20 is thereby adapted to easily fit over the outer surface 18 of the tube 12 and be crimped securely at the desired central location without removing any radioactive coating on the outer surface 16 of the tube. The collar 20 is also preferably provided with tapered edges 28, 30 to facilitate movement of the two halves 34, 36, of the capsule 22 over the collar. The capsule halves 34, 36 are preferably machined or etched from titanium or another radiolucent material, although, if desired, the capsule halves may be made as drawn tubes which are provided with thick bases (closed ends 38, 40) from which engaging means or connectors can be machined or etched. Thus, each half 34, 36 includes a closed end 38, 40 and an open end 42, 44, respectively; and each closed end 38, 40 is preferably provided with an engaging means or connector 46, 48, described in more detail below. In assembly, the halves 34, 36 of the capsule 22 are positioned over the tube 12 with the open ends 42, 44 of the halves guided by the tapered edges 28, 30 to form a preferably tight interference fit with the collar 20. The open ends 42, 44 are butt welded about the collar 20 to seal the capsule 22, and the collar protects the contents of the capsule from the heat of welding.

Alternatively, the collar 20 may be formed with the slit and welded to one capsule half, e.g., half 34. The tube 12 can then be slid into the collar (without forming a friction fit) and the other capsule half, e.g., half 36, can be positioned over the collar 20 and butt welded with the capsule half 34.

Figure 2:
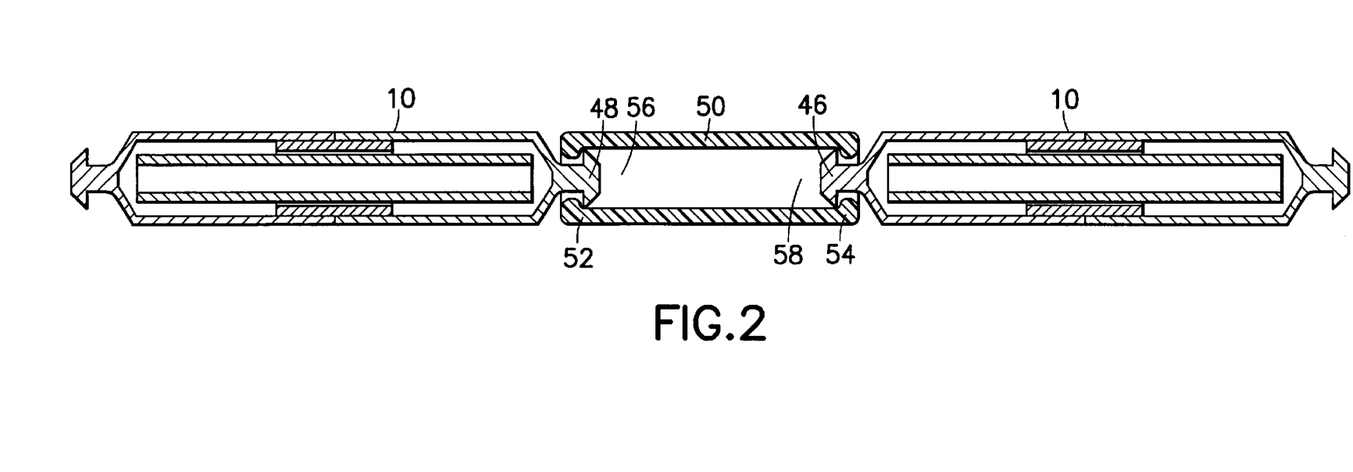
FIGS. 2 through 5 are enlarged schematic longitudinal sections of four embodiments of two therapeutic seeds with different connector elements according to the invention in conjunction with various links.

Turning now to FIG. 2, according to a preferred aspect of the invention, the engaging means or connectors 46, 48 are barbs and are adapted to either mate with a spacing link 50 to couple a plurality of seeds together, or to engage surrounding tissue in a manner which will not easily permit movement of the seed in the tissue. The barbs, therefore, facilitate proper relative spacing of the seeds at the implant site within the human body. When utilized, the spacing link 50 is preferably a stiff, optionally hollow, bioabsorbable polymer, e.g., polydioxanone, poly(l-lactide-co-trimethylene carbonate), d,l-lactide/caprolactone or 50:50 d,l-polylactide co-glycolide polymer, and includes female mating structure 52, 54 at each of its ends 56, 58 adapted to mate, e.g., via an interlock, with the connectors 46, 48 of the seeds 10. According to the invention, seeds are linked together prior to loading them into an injection needle so that when they are deployed, they will remain connected to each other. Links 50 of different length may be provided so that the practitioner may determine in advance of the procedure how far apart adjacent seeds will be spaced. Alternatively, spacers of desired lengths may be provided between the barbed seeds. As yet another alternative, links may be manufactured in an insert molding process where slugs of polymer are placed in a Teflon coated or other tube between the seeds (e.g., in a seed-slug-seed-slug-seed type of pattern), heat is provided to at least partially melt the slugs, and pressure is applied to the end seeds. The resulting link/spacer will be substantially solid, but will mate with the connectors of the seeds.

Figure 3:
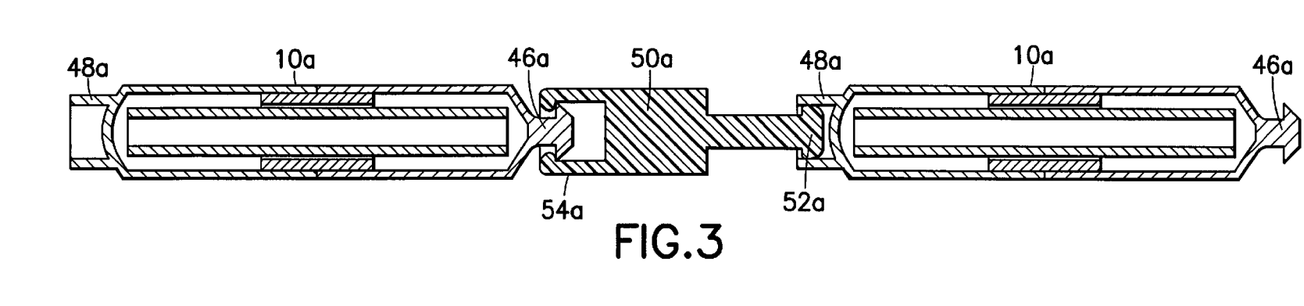

Turning now to FIGS. 3 through 11, it will be appreciated that other engaging means or connectors can be provided to the seed. In addition, other mating structures can be provided to the link to mate with the connectors. Referring to FIG. 3, according to a second example, each seed 10a may include one end having a machined or etched male annular barb-like connector 46a and an opposite end having a female connector 48a. The link 50a provided for such a seed 10a would likewise have a male barb-like mating structure and a female mating structure, 52a, 54a, respectively, for interlockingly mating with the connectors 48a, 46a of the seeds 10a (connector 48a deforming mating structure 52a in interlocking engagement). It will also be appreciated that two such seeds 10a may be coupled together by coupling a male mating structure 46a of one seed with a female mating structure 48a of another seed. Alternatively, because the seeds are provided with barbs, they may be used without links.

Figure 4:
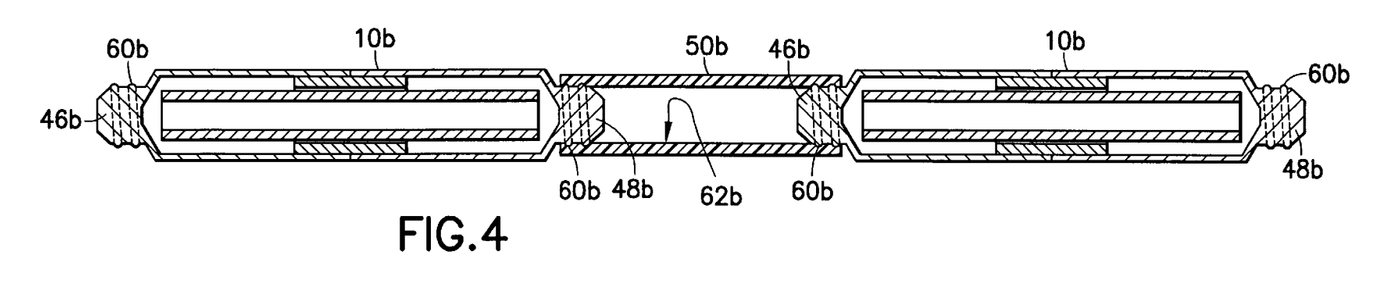

Referring to FIG. 4, according to a third example, each seed 10b may include male connectors 46b, 48b having threads 60b thereon. The spacing link 50b is substantially tubular, having an inner diameter sized to permit the threads 60b to deform the inner surface 62b of the tubular link 50b and interlock therewith (i.e., form a positive resistive engagement).

Figure 5:
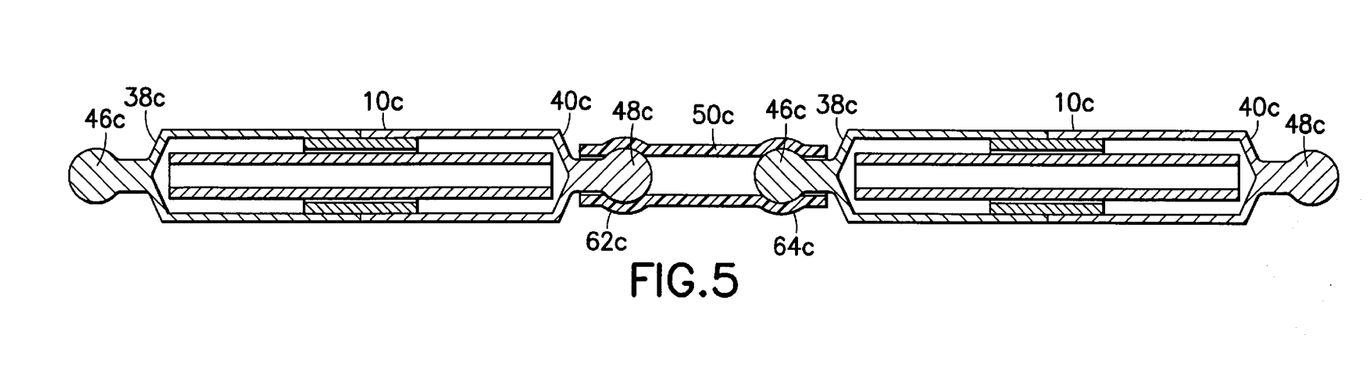

Turning to FIG. 5, according to a fourth example, the closed ends 38c, 40c of each seed 10c are provided with radiolucent ball joints 46c, 48c. The link 50c is preferably a tube of bioabsorbable material having ends 62c, 64c sized to be forced over and conform to the ball. Once the ball joints 46c, 48c are engaged within the ends 62c, 64c of the link, they cannot easily be withdrawn, but can withstand substantial tensile force.

Figure 6:
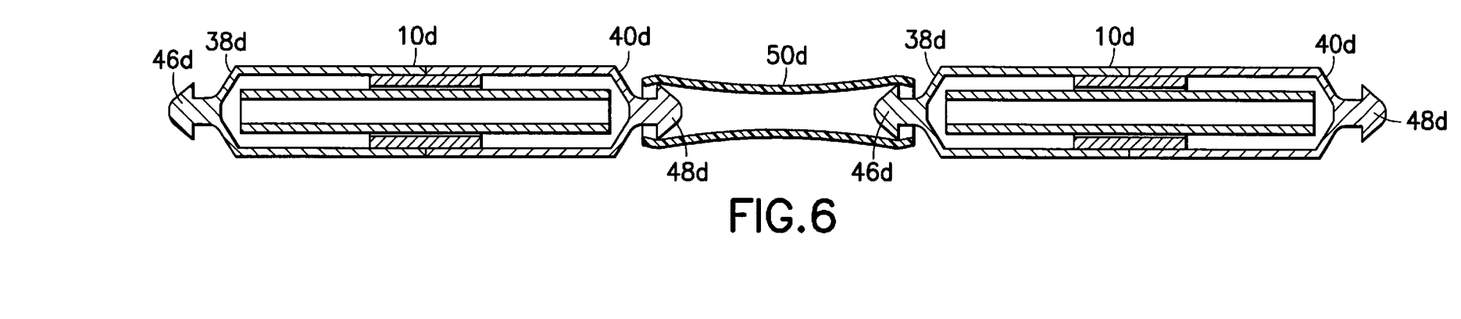
FIG. 6 is an enlarged schematic longitudinal section of a fifth embodiment of two therapeutic seeds with a linking element.
Figure 7:
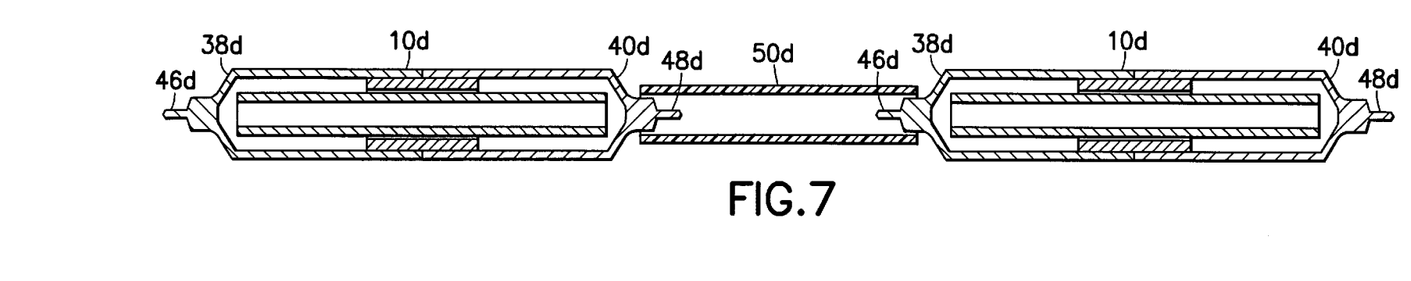
FIG. 7 is a view similar to FIG. 6, axially rotated 90° relative to FIG. 6, of the fifth embodiment of two therapeutic seeds with a linking element.

Referring now to FIGS. 6 and 7, according to a fifth example, the closed ends 38d, 40d of each seed 10d are provided with flattened barbs 46d, 48d. The link 50d (when utilized) is preferably substantially tubular, and may permit some flexing (as shown in FIG. 6) or may be substantially rigid. The flattened barbs 46d, 48d are sized to deform or engage the tubular link 50d at the points of contact, thereby providing substantially two locations of relatively high interference, rather than the distributed annular interference of the fourth example (FIG. 5). Alternatively, the barbed seed may be used without a link, as the barb will engage tissue in a manner which will substantially fix the seed at an implant location.

Figure 8:
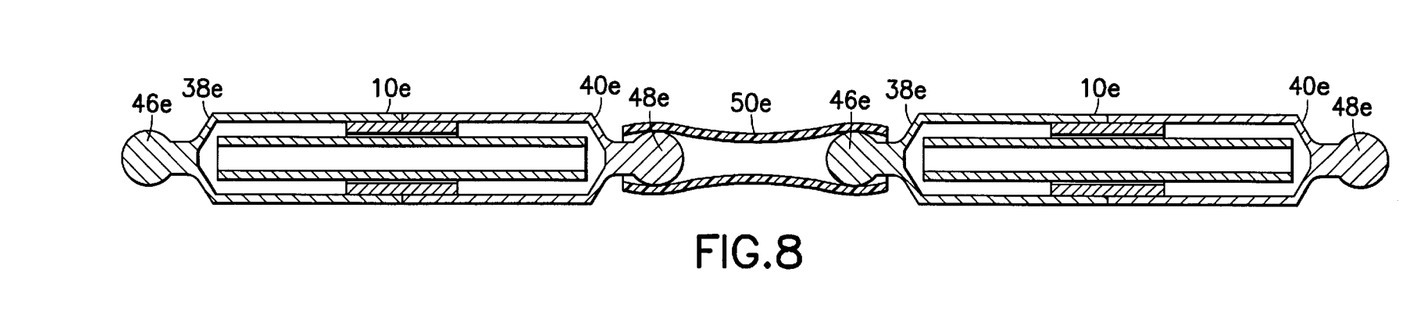
FIG. 8 is an enlarged schematic longitudinal section of a sixth embodiment of two therapeutic seeds with a linking element.
Figure 9:
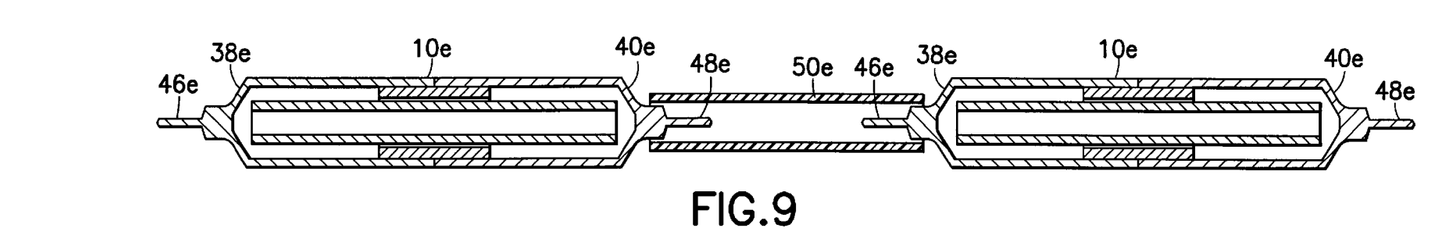
FIG. 9 is a view similar to FIG. 8, axially rotated 90° relative to FIG. 8, of the sixth embodiment of two therapeutic seeds with a linking element.

Turning now to FIGS. 8 and 9, according to a sixth example, the closed ends 38e, 40e of each seed 10e are provided with discs 46e, 48e. The link 50e is preferably substantially tubular, and the discs 46e, 48e engage and/or deform the link 50e substantially as described with respect to the fifth example.

Figures 10, 11:
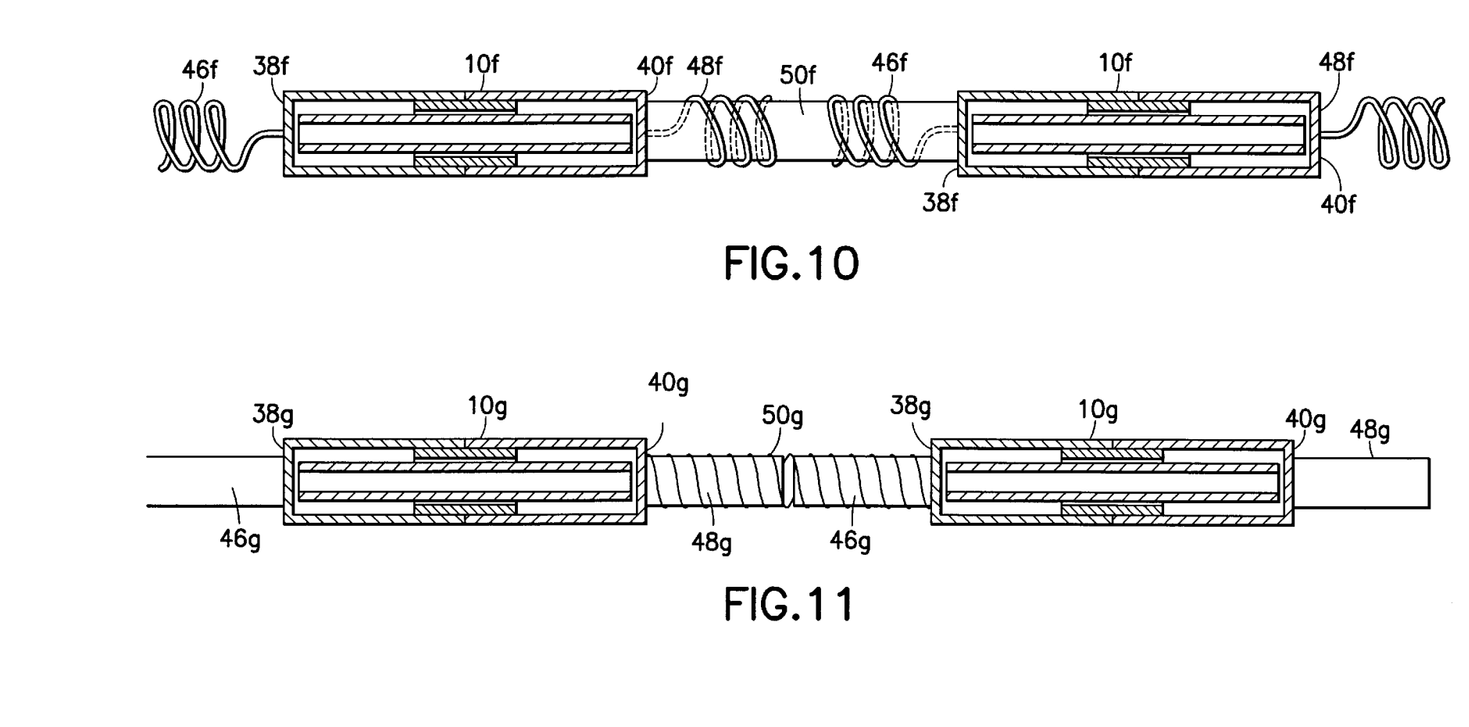
FIGS. 10 and 11 are enlarged schematic longitudinal sections of seventh and eighth embodiments of two therapeutic seeds with different connector elements according to the invention in conjunction with links.

Referring now to FIG. 10, according to a seventh example, coil-like engagement seeds or connectors 46f, 48f extend from the closed ends 38f, 40f of each seed 10f. Two facing coil-like connectors 46f, 48f on adjacent seeds 10f are axially compressed to increase their interior diameters. When used, a rod-like bioabsorbable link 50f is positioned at least partially within each connector, preferably such that the ends of the link are positioned adjacent the closed ends 38f, 40f of the seed 10f. The connectors 46f, 48f are then released from axial compression such that they grip the link 50f. It will be appreciated that when the seeds are subject to tensile force, the coil connectors constrict in diameter, enhancing their grip on the link.

Turning now to FIG. 11, according to an eighth example, the closed ends 38g, 40g of each seed 10g are provided with rod-like extensions 46g, 48g, and the link 50g is a preferably bioabsorbable radiolucent coil having a natural inner diameter smaller than the outer diameter of the extensions. The coil link 50g can be axially compressed to at least partially receive the rod-like extensions 46g, 48g on the opposing ends of two seeds 10g, and axially released to securely grip the extensions. The eighth example thereby operates similarly to the seventh example.

In each example, the seed connector is preferably adapted to retain connection to the link, when used, even when subject to some tensile force. Additionally, a plurality of coupled seeds and links preferably will not substantially buckle when subject to compressive force. These preferred aspects of the seeds when used with the links preferably permit repositioning of the seeds at or adjacent the site of implantation from the proximal end of a chain of seeds and links. Moreover, the seed connectors and links are all preferably radiolucent. It will be appreciated that relatively long chains comprising multiple seeds and links can be formed and delivered without interfering with the isotopic radiation distribution of individual seeds. Alternatively, where the seeds have barbs, a plurality of seeds may be loaded with bioabsorbable spacers therebetween.

A plurality of seeds 10 coupled together by the links 50 may be loaded together into a delivery device, and delivered together to the physiological site at which radiation therapy is desired. In addition, with the bioabsorbable links, the seeds may be provided to the site in a desired relative spacing in accord with the prescriptive dose of radiation to applied. In addition, as the links are preferably bioabsorbable, they will be absorbed by the human body at the physiological site, leaving the seeds separated.

Figure 12:
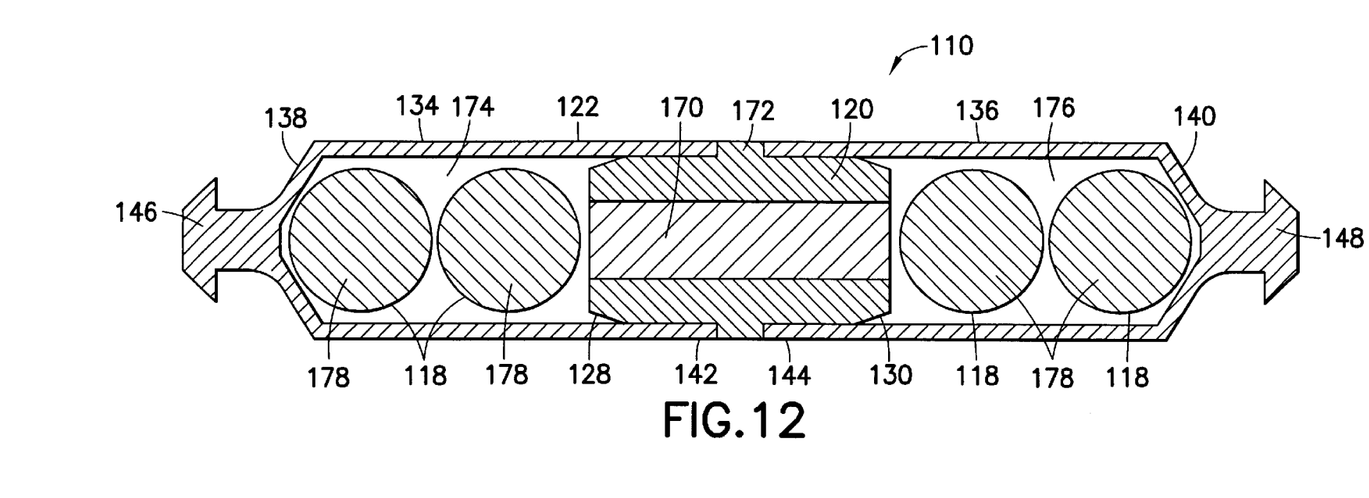
FIG. 12 is an enlarged schematic longitudinal section of a radioactive therapeutic seed according to a second embodiment of the invention.

Turning now to FIG. 12, a second embodiment of a therapeutic seed 110 according to the invention is shown. The seed 110 includes a preferably titanium capsule 122 defined by two halves 134, 136, each having a closed end 138, 140 provided with an engagement means or connector 146, 148, as described above, an open end 142, 144, and an interior portion 174, 176. In the interior portion 174, 176 of each half 134, 136 of the capsule 122, isotope bearing structures 178 are provided. Preferably, the isotope bearing structures 178 are one or more radiolucent particles, preferably made from titanium, aluminum or glass, and preferably spherically shaped. The particles 178 are provided with a thin coating of silver over which the isotope 118 is provided. The two halves 134, 136 of the capsule are welded about a plug 120. The plug 120 is preferably a relatively thick titanium tube having an axial radiopaque marker 170 therein. The plug 120 preferably includes tapered ends 128, 130 to facilitate positioning the open ends 142, 144 thereover, and a central circumferential ridge 172 against which the open ends of the two halves of the capsule are butt against and welded thereto.

Figure 13:
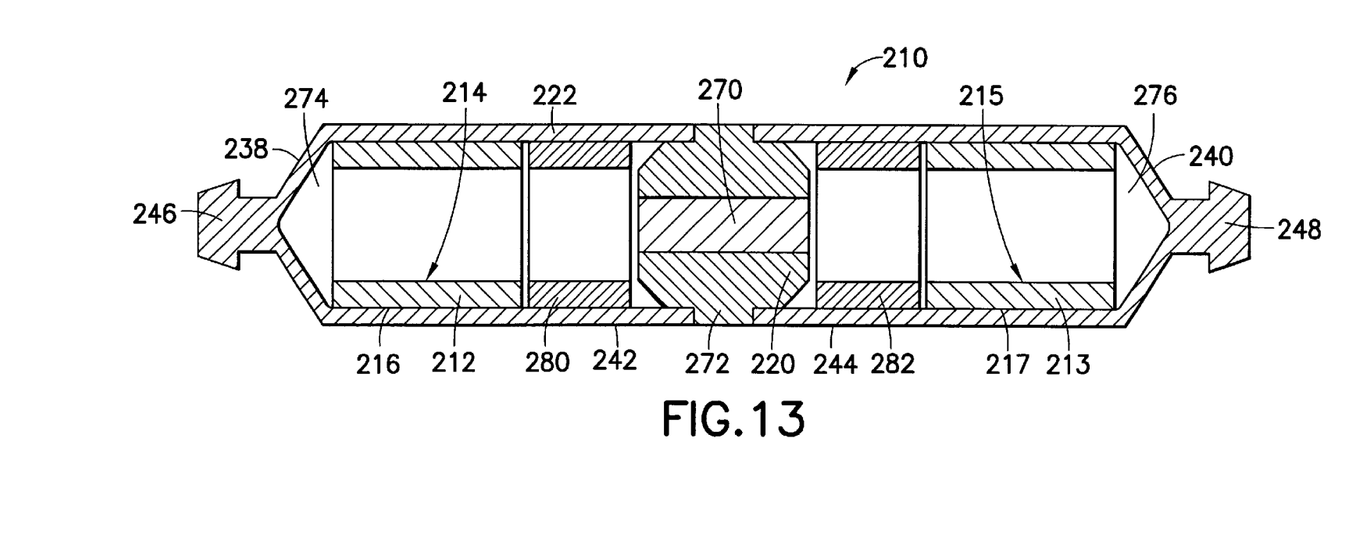
FIG. 13 is an enlarged schematic longitudinal section of a radioactive therapeutic seed according to a third embodiment of the invention.

Referring now to FIG. 13, a third embodiment of a therapeutic seed 210 according to the invention is shown. The seed 210 includes a radiolucent titanium capsule 222 defined by two halves 234, 236, each having a closed end 238, 240 provided with an engagement means 246, 248, as described above, an open end 242, 244, and an interior portion 274, 276. In the interior portion 274, 276 of each half 234, 236 of the capsule 222, a silver tube 212, 213 is provided. Each tube 212, 213 is preferably 0.025 inch in length and preferably has a wall thickness of 0.004 inch. The interior surfaces 214, 215 and the exterior surfaces 215, 217 of the tubes are coated with I-125. As the tubes 212, 213 may be shorter than the length of the interior portion 274, 276, spacers 280, 282 may be provided in the interior portion 274, 276 to prevent relative movement of the tubes 212, 213 within the capsule 222. The two halves 234, 236 of the capsule are welded about a plug 220. The plug 220 is preferably a titanium tube having a radiopaque marker 270 therein. Additionally or alternatively, the marker may be diamagnetic. The plug 220 preferably includes tapered ends 228, 230 to facilitate positioning the open ends 242, 244 thereover, and a central circumferential ridge 272 against which the open ends of the two halves of the capsule are butt against and welded thereto.

There have been described and illustrated herein several embodiments of a radioactive therapeutic seed. While particular embodiments of the invention have been described, it is not intended that the invention be limited thereto, as it is intended that the invention be as broad in scope as the art will allow and that the specification be read likewise. For example, those skilled in the art will appreciated that certain features of one embodiment may be combined with features of another embodiment to provide yet additional embodiments. Also, while a variety of male connectors have been described, it will be appreciated that other male connectors may be used in combination or in the alternative. In addition, while each capsule is preferably formed from two halves, it will be appreciated that the two parts forming the capsule need not be halves, e.g., one part can be one-third the length of the capsule and the other part can be two-thirds the length of the capsule. Also, while one type of MRI-visible substance has been disclosed, other MRI-visible substances may alternatively be used. Furthermore, while the isotope bearing surface has been disclosed as preferably including both the inner and outer surfaces, it will be appreciated that just the outer surfaces may be used as the isotope bearing surface, though it is believed that the embodiments as described provide the most isotropic radiation distribution. Also, while the spacing link is preferably bioabsorbable, it will be appreciated that the spacing link is not required to be bioabsorbable. It will therefore be appreciated by those skilled in the art that yet other modifications could be made to the provided invention without deviating from its spirit and scope as so claimed.

What is claimed is:

1. A radioactive therapeutic seed, comprising:
   a) a carrier structure carrying a radioactive isotope;
   b) a collar member provided about said carrier structure; and c) a capsule having two parts, each part including a closed end and an open end, said carrier structure with said collar member being disposed in said capsule, with said open ends of said two parts of said capsule being sealed together over said collar member.

2. A radioactive therapeutic seed according to claim 1, wherein: said parts do not overlap each other.

3. A radioactive therapeutic seed according to claim 1, wherein:
said carrier structure has an outer surface, and said radioactive isotope is provided on said outer surface.

4. A radioactive therapeutic seed according to claim 3, wherein:
a silver layer is provided on said outer surface under said radioactive isotope.

5. A radioactive therapeutic seed according to claim 1, wherein:
said collar member is made from titanium or gold.

6. A radioactive therapeutic seed according to claim 1, wherein:
said collar member is made from an MRI-visible substance.

7. A radioactive therapeutic seed according to claim 1, wherein:
said two parts of said capsule are sealed together over said collar member with a weld.

8. A radioactive therapeutic seed according to claim 1, wherein:
said two parts each comprise substantially one half of said capsule.

9. A radioactive therapeutic seed according to claim 1, wherein:
at least one of said closed ends of said capsule is provided with a structure adapted to engage a spacer or tissue in which the capsule is situated.

10. A radioactive therapeutic seed according to claim 1, wherein:
said carrier structure is a tube.

11. A radioactive therapeutic seed according to claim 10, wherein:
said tube has an inner surface and an outer surface and s aid radioactive isotope is provided on both said inner surface and said outer surface of said tube.

12. A radioactive therapeutic seed comprising:
a) at least two carrier structures each carrying a radioactive isotope;
b) a plug member;
c) a capsule having two parts, each part including a closed end, an open end, and an interior, at least one of said at least two carrier structures being provided in said interior of each part, with said open ends of said two parts of said capsule being sealed together about said plug member; and
d) an MRI-visible marker,
wherein said plug is provided with a hollow, and said marker is provided in said hollow.

13. A radioactive therapeutic seed comprising:
a) at least two carrier structures each carrying a radioactive isotope;
b) a plug member;
c) a capsule having two parts, each part including a closed end, an open end, and an interior, at least one of said at least two carrier structures being provided in said interior of each part, with said open ends of said two parts of said capsule being sealed together about said plug member; and
d) two radiolucent spacing members, one of each being provided in each said interior of a respective part of said capsule between said carrier structure and said plug.

14. A radioactive therapeutic seed comprising:
a) at least two carrier structures each carrying a radioactive isotope;
b) a plug member; and
c) a capsule having two parts, each part including a closed end, an open end, and an interior, at least one of said at least two carrier structures being provided in said interior of each part, with said open ends of said two parts of said capsule being sealed together about said plug member,
wherein each said carrier structure is a tube.

15. A radioactive therapeutic seed according to claim 14, wherein:
each said tube has an interior surface and an exterior surface, and said radioactive isotope is provided on said interior and exterior surfaces.

16. A radioactive therapeutic seed according to claim 14, wherein:
said tube is made from silver.

17. A radioactive therapeutic seed comprising:
a) at least two carrier structures each carrying a radioactive isotope;
b) a plug member; and
c) a capsule having two parts, each part including a closed end, an open end, and an interior, at least one of said at least two carrier structures being provided in said interior of each part, with said open ends of said two parts of said capsule being sealed together about said plug member,
wherein said closed ends of said capsule are each provided with an engagement structure adapted to engage a spacer or tissue in which the capsule is situated wherein said plug includes tapered ends.

18. A radioactive therapeutic seed comprising:
a) at least two carrier structures each carrying a radioactive isotope;
b) a plug member; and
c) a capsule having two parts, each part including a closed end, an open end, and an interior, at least one of said at least two carrier structures being provided in said interior of each part, with said open ends of said two parts of said capsule being sealed together about said plug member,
wherein said closed ends of said capsule are each provided with an engagement structure adapted to engage a spacer or tissue in which the capsule is situated.

19. A radioactive therapeutic seed, comprising:
a capsule provided with a radioactive isotope; and
a paramagnetic or diamagnetic MRI-visible marker coupled to said capsule or provided in said capsule.

20. A radioactive therapeutic seed, comprising:
a capsule having a first end having integral therewith-a non-absorbable male engagement structure adapted to engage a spacer or tissue in which the capsule is situated, said capsule provided with a radioactive isotope.

21. A radioactive therapeutic seed according to claim 20, wherein: said capsule is made of a metal or metal alloy.

22. A radioactive therapeutic seed according to claim 20, wherein:
said radioactive isotope is provided on a carrier structure and said carrier structure is provided in said capsule.

23. A radioactive therapeutic seed according to claim 20, wherein:
said capsule has a second end having one of a second male engagement structure and a female engagement structure.

24. A radioactive therapeutic seed according to claim 20, wherein:
said male engagement structure comprises a barb.

25. A radioactive therapeutic seed according to claim 20, wherein:
said male engagement structure comprises a disc.

26. A radioactive therapeutic seed according to claim 20, wherein:
said male engagement structure includes at least one thread.

27. A radioactive therapeutic seed according to claim 20, wherein:
said male engagement structure includes a ball.

28. A radioactive therapeutic seed, comprising:
a metal capsule having first and second ends and a barbed male member at at least one said first and second ends, said capsule provided with a radioactive isotope.

29. A radioactive therapeutic seed, comprising:
a metal capsule having first and second ends, said capsule having a machined or etched male member at at least one of said first and second ends, said capsule provided with a radioactive isotope.

30. A radioactive therapeutic seed system, comprising:
a) at least two seeds, each seed comprising a biocompatible capsule having a first end, a second end, and a body structure therebetween, said first end having a male connecting structure different from said body structure and said second end having one of a second male connecting structure and a female connecting structure different from said body structure, said capsule provided with a radioactive isotope; and
b) a discrete linking member interlocking with said first end of one seed and said second end of another seed.

31. A radioactive therapeutic seed system according to claim 30, wherein:
said linking member is bioabsorbable.

32. A radioactive therapeutic seed system according to claim 30, wherein:
said linking member is tubular.

33. A radioactive therapeutic seed system according to claim 30, wherein:
said linking member is an axially compressible coil.

34. A radioactive therapeutic seed system according to claim 30, wherein:
said connectors and said linking member are radiolucent.

35. A radioactive therapeutic seed system according to claim 30, wherein:
said linking member is substantially non-hollow.

36. A radioactive therapeutic seed system according to claim 30, wherein:
said linking member is an insert molded polymer.

37. A radioactive therapeutic seed system, comprising:
a) at least two seeds, each seed comprising a biocompatible capsule having first and second ends each provided with a connecting structure, said capsule provided with a radioactive isotope; and
b) a discrete linking member interlocking with said connecting structure of one seed and said connecting structure of another seed, said linking member including means for retaining said one seed and said other seed together when subjecting said one seed and said other seed to a tensile force and for resisting buckling of said one seed relative to said other seed when subjecting said one seed and said other seed to a compressive force.

38. A radioactive therapeutic seed system according to claim 37, wherein:
said linking member is a bioabsorbable rod.

39. A radioactive therapeutic seed system, comprising:
a) at least two seeds, each seed comprising
i) a biocompatible capsule having a first end and a second end, one of said first and second ends having a connecting structure in the form a coil, and
ii) a radioactive isotope disposed in said capsule; and
b) a linking member interlocking to be engaged by said connecting structure of one seed and said connecting structure of another seed.

* * * * *